United States Patent [19]

Linden

[11] 4,311,910
[45] Jan. 19, 1982

[54] FIELD DESORPTION IONIZATION

[76] Inventor: Hans B. Linden, Dulonweg 2, 2800 Bremen 61, Fed. Rep. of Germany

[21] Appl. No.: 137,255

[22] Filed: Apr. 3, 1980

[51] Int. Cl.³ .............................................. H01J 27/00
[52] U.S. Cl. ............................................. 250/423 R
[58] Field of Search ............... 250/281, 282, 288, 289, 250/423 R, 423 F, 424, 440, 442, 457

[56] References Cited

U.S. PATENT DOCUMENTS

| | | | |
|---|---|---|---|
| 3,308,292 | 3/1967 | Ardenne | 250/423 |
| 3,720,829 | 3/1973 | Palmberg | 250/440 |
| 4,178,507 | 12/1979 | Brunnée et al. | 250/282 |

OTHER PUBLICATIONS

"Purification, Wet Processes Determination of Structure", Korte, *Methodicum Chimicum*, vol. 1, Part A, 1974, pp. 493–504.
"High-rate Growth of Dendrites on Thin Wire Anodes for Field Desorption Mass Spectrometry", Linden et al., *J. Physics E: Sci Instaim.;* vol. 11, 1978, pp. 1033–1036.
On the Mechanism of Cathodic Growth on Tungsten Needles by Decomposition of Hexacarbonyltungsten under High Field Conditions", Linden et al., *App. Physics,* 22, 1780, pp. 83–87.
"New Sample Supply Tech. for Field Desorption Mass Spectrometry", Linden et al., *J. of Physics E: Sci. Inst.,* vol. 10, 1977, pp. 657–660.

*Primary Examiner*—Bruce C. Anderson
*Attorney, Agent, or Firm*—Smyth, Pavitt, Siegemund & Martella

[57] ABSTRACT

The requisite process chambers for field desorption ionization are annularly arranged and cooperate with electrodes on the inside. Individual electrodes are cyclically and in steps juxtaposed to the process chambers so that the various steps are simultaneously carried out on different electrodes. After a cycle, all electrodes have faced all of the chambers. Alternatively, a single wire is segmentwise placed adjacent to the chambers. The process steps are, in each instance: activating the electrode (or a wire segment); depositing an analyzing substance; ionization; and cleaning.

8 Claims, 3 Drawing Figures

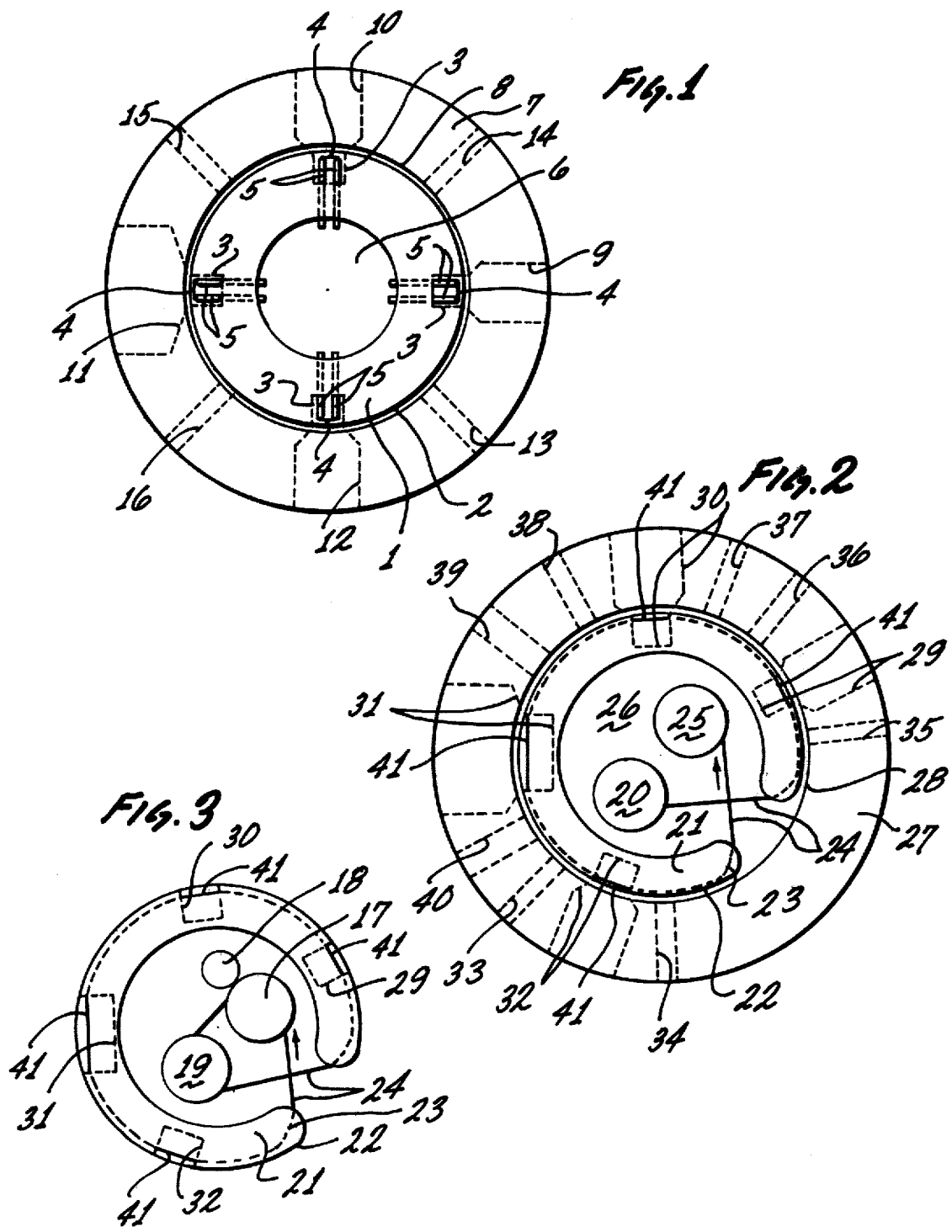

FIELD DESORPTION IONIZATION

BACKGROUND OF THE INVENTION

The present invention relates to a method and apparatus for coordinating, in time and space, the process sequence of field desorption ionization.

Ionization by means of electric field desorption is practiced in the field of mass spectrometrie, particularly for ionizing thermo-instable substances which are not very volatile. The known method in this regard is very time-consuming and requires extensive intervention and manipulation by operating personnel.

The known method requires preparation of electrodes, setting up the field. This preparation involves chemical activation for the growth of dendrites in a special apparatus, a process which requires at least ten minutes, but possibly also several hours, depending upon process particulars. Following this activation, the field electrode has to be taken out of the special activating device, for being loaded with the material to be investigated and analyzed. Next, the loaded electrode has to be inserted into a source of ions, including a high vacuum chamber. The test is conducted in that chamber. Subsequently, the electrode has to be removed from this test chamber; and after thorough cleaning, the electrode may be recycled and used anew.

It can readily be seen that this field desorption ionization method involves a rather long measuring cycle, beginning with electrode activation and ending with the cleaning. Many steps and manipulations are required to be carried out by human operators; and as such, this method is not amenable to complete automation.

Also, it is not feasible to couple devices involved in the process directly to sources furnishing the material to be analyzed. Such sources may operate on an intermittent basis, e.g., a fraction collector, or continuously, such as a high-pressure liquid chromatograph.

DESCRIPTION OF THE INVENTION

It is an object of the present invention to improve field desorption ionization in a manner rendering the processes amenable to automation.

In accordance with the preferred embodiment of the present invention, it is suggested to carry out the requisite process steps concurrently on different portions of an electrode means which is stepwise moved past the process chambers. The process steps in question are: electrode activating; depositing substance to be analyzed; ionization; and cleaning. In the preferred form, the process chambers are annularly arranged; and the electrodes, either individual ones or a continuous wire, are stepwise moved along an annular path past these chambers. Thus, any wire segment or electrode is stepwise and sequentially juxtaposed to all process chambers, while each chamber faces a different electrode or wire segment and performs its processing step thereupon. The electrode positioning is carried out in a manner which effectively seals each process chamber from the other chambers. The electrode or wire carrier has certain concave or recessed portions for holding the electrodes or guiding the wire; and these recess portions complete, in space, in each instance the process chamber, the major portion of each process chamber being in an annular case inside which the electrode means moves.

DESCRIPTION OF THE DRAWINGS

FIG. 1 is a schematic front view of an apparatus for practicing the inventive method in accordance with the best mode;

FIG. 2 is a similar schematic view of a modified apparatus; and

FIG. 3 shows a detail of FIG. 2, but includes a modification.

Proceeding now to the detailed description of the drawings, FIG. 1 illustrates a tubular, cylindrical electrode holder or carrier 1, being made, e.g., from ceramic and having an outer cylindrical surface 2 which, so to speak, functions as an endless carrier. The cylindrical electrode holder 1 is provided with radial pockets or recesses 3 for holding electrodes. Presently, field electrodes 4 are placed into these pockets; arms 5 of the electrodes respectively extend into the interior of the pockets. These arms 5 may be connected to terminals in the pockets to permit individual current feeding through the respective electrode.

An outer, tubular case 7 has an interior bore 6 defined by a cylindrical wall 8, being dimensioned to be in sliding contact with the outer, peripheral surface 2 of the electrode holder 1. This means that the carrier or holder 1 can be axially inserted into case 7, and the holder 1 can also rotate therein. However, there should be no noticeable gap (the illustration shows a gap only for the reason of permitting distinction amount the concentric surfaces involved).

The case 7 is provided with a plurality of bores, 9, through 16, which differ in contour and dimensions among each other; they have different functions and purpose. Basically, there are four relatively large bores (9, 10, 11 and 12) which are spaced by 90 degrees to each other, commensurate with the 90-degree spacing of the four pockets 3 in carrier 1. The figure shows particularly these pockets in direct alignment with the four bores 9 through 12. These latter bores constitute process chambers, or, more accurately, a major portion for such a process chamber; the respective pocket 3 facing it completes the chamber in each instance. It can thus be seen that four different process steps can be carried out simultaneously on four different electrodes.

The bores 13, 14, 15 and 16 are respectively interspaced between the process chamber bores and serve as venting ducts. As will be described more fully below, the electrode holder 1 is rotated by 90 degrees in between sequential process steps as performed on all of the electrodes. Each pocket 3 and its electrode, while moving from one process chamber to the next, will pass one of the venting bores, 13 to 16, so that gas residue can be sucked off, before the respective electrode is subjected to the next process step.

Turning now to process specifics, the particular electrode in the pocket facing process chamber 9 is presumed to be clean, and chamber 9 is provided for activating the electrode it contains and faces. In particular, chamber 9 causes depositing and precipitation of dendi tric microneedles, from a carrier gas onto the electrode. Precipitation and depositing details as well as the current leads connected to the electrode have been omitted, the latter for the sake of clarity, the former because the process details of activating follows conventional lines.

Simultaneously with the activating step in chamber 9, liquid analyzer substances are dropped onto the particular electrode 4 facing chamber 10. The electrode has previously been activated in chamber 9. The residence time of the electrode in (or adjacent to) chamber 10 permits the solvent of the analyzer substance to evaporate, and solid substance remains deposited on the dendrites of the electrode.

Simultaneously with the foregoing, another electrode is processed in chamber 11. That particular electrode has arrived at adjacent chamber 11, carrying an analyzer substance on its dendride needles. This substance is now subjected to ionization by means of field desorption ionization, or by means of a laser, or by chemical reaction, or any other suitable solid-body-type ionization method. It should be noted that the pockets 3 may include additional means needed in this or that chamber for completion of the equipment needed in the process. Presently, pockets 3 may contain means for electronic impact ionization, or a portion of such equipment, the remaining portion being in chamber 11. In the case of chemical ionization, appropriate means or a portion thereof may be included in pockets 3.

Bore 12, the last one of the process chambers, includes equipment for cleaning the respective adjacently positioned electrodes to remove therefrom any substance and residue as well as the dendritic microneedles. Cleaning can be carried out mechanically by stripping the dendrites off the electrode. Preferred is, however, burning the dendrites off by means of an electric discharge. This is the reason for providing separate circuit connection to the electrodes so that they can be energized individually for and in each of the process chambers.

The electrode holder 1 remains in a particular position, in which the electrodes face the process chambers, for about ten minutes. During that period, one electrode is cleaned (chamber 12); another one is activated (chamber 9); a third one receives a deposit of substances to be analyzed (chamber 10); and the fourth one (chamber 11) is ionized. Conversely, each electrode is subjected to all four of the process steps after holder 1 has been rotated by four steps, at a total of 360 degrees, i.e. a complete revolution. This could be termed a process cycle in which any one of the electrodes undergoes all four steps.

It is repeated once more that during each 90-degree turn each of the four electrodes passes one of the four venting ducts 13 to 16. Suction may be provided to all of these ducts in order to purge all electrode-holding pockets from any and all residue of the respective previous process step just completed and prior to placing the electrodes into the next process chamber.

The tubular arrangement comprised of the two tubular devices 1 and 7 should be closed on each axial end during the process. This poses no problem since the tube 7 remains stationary. One of the axial covers must be provided for a sealed feedthrough of the rotation to be imparted upon tube 1. However, drive means could be included in the enclosure, and only current leads are run through any wall.

The ducts 13 to 16 are shown schematically; they may be interconnected and suitably manifolded, leading to a single duct which is connected to a suction pump.

The various processes are controlled from the outside, the various process chambers, 9 to 12, being suitably connected to their respective feeder equipment.

The various processes are independently controlled; and upon termination of all (one step per chamber), tube 1 will be turned. This may occur in regular intervals, e.g., in 10-minute periods or directly upon completion of the longest lasting one of the processes.

The example shown in FIGS. 2 and 3 differs from the previous one in structural details, but not in principle. FIG. 2 shows, in particular, a cylindrical outer body or case 27, having a plurality of process chambers 29, 30, 31, and 32; but they are not angularly equidistantly spaced from each other. Nevertheless, they are provided for their activating, depositing, ionizing, and cleaning functions.

The cylindrical rotary carrier 1 in FIG. 1 has been replaced by a stationary holder 21 (see also FIG. 3), and the individual electrodes are replaced by a single wire 24. In FIG. 2, the wire is unreeled from a spool 20 and rewound on a take-up spool 25. In FIG. 3, the wire is of an endless configuration, being moved by a driven pulley or capstan 19 and guided by a pulley 17. In either case, the wire 24 runs in a more than 270-degree but less than 360-degree arc in holder 21. The wire is particularly guided and held in a peripheral groove 23 of body 21. In any instant, a segment or portion 41 of that wire faces a process chamber. Thus, four different segments face simultaneously the four process chambers 29 through 32.

As stated, these process chambers are not equidistantly spaced from each other. The spacings must be such that each of them is approximately an integral multiple of the segment length 41.

It can readily be seen that adjacent segments of the wire may be used; and each segment may undergo a certain waiting period before being subjected to a next process step. Take the state as depicted in FIG. 2 or 3. A certain segment of the wire 24 faces activation chamber 29 to receive dendrites. Another segment faces chamber 30 and analyzing substance is deposited thereon. Another wire segment carrying dendrite and deposits is ionized in chamber 31 and a fourth segment is being cleaned in chamber 32. Upon completion of all four concurring and overlapping process steps, the wire is shifted by a segment length (or a little more if that is desired). This places all segments just worked upon into a waiting state, in between chambers, while other portions of the wire which had been "waiting" earlier are now processed. After a few, or several, such cycles, three of the segments originally considered will again be processed, each undergoing the next step type of process, etc. It can, thus, be seen that the movement of the wire is carried out in smaller steps as compared with the 90-degree rotation of FIG. 1 needed for each change. Also, the device is simpler than in FIG. 1, but the several wire segments are necessarily electrically interconnected so that participation of the wire as a current conductor is limited.

The body 27 has also a plurality of venting bores 33 through 38 which are manifolded and connected to an exhaust pump system to make sure that the process chamber will not receive the wrong kind of evaporation being residue from the previous process step. There are two additional bores, 39 and 40, which are connected to a different pump. These two bores are disposed next to chamber 31 and maintain a high vacuum therein, overcoming particularly any leakage via notch 23. Such a vacuum is usually required for an effective ionization. The peripheral wall 22 of body 21 engages tightly the inside wall 28 of body 27 to ensure tight sealing of the process chambers from each other.

The carrier 21 is shifted axially into bore 26 defined by the tubular or annular case or body 27, particularly prior to start-up. Removal and replacement may become necessary after some time has elapsed for changing the wire (FIG. 3) or for placing a spool with a fresh wire into the body as per FIG. 2. The axial openings of bore 26 are, of course, tightly sealed during operation. One or both axial end covers (not shown) will be provided with a feedthrough shaft, gear, or the like, to impart rotation upon the take-up spool 25, or capstan 17, in FIG. 3.

It can readily be seen that the annular arrangement of the various process means as cooperating with a rotating electrode means, single wire, or plural discrete electrodes also operating on an annular path, permits immediate and direct automation of the process. The process steps proper are controlled and operated from the outside, i.e., along the periphery of case 7 or 27. In each instance, these various processes are independently performed and controlled; they are merely coordinated in time, i.e., synchronized with each other.

The invention is not limited to the embodiments described above; but all changes and modifications thereof, not constituting departures from the spirit and scope of the invention, are intended to be included.

I claim:

1. Apparatus for carrying out field desorption ionization, comprising:
    an annular case having a plurality of radially extending, separated process chambers including (i) a first chamber for activating an electrode, (ii) a second chamber for depositing analyzing substance onto an activated electrode, (iii) a third chamber for ionizing the substance by means of field desorption ionization, and (iv) a fourth chamber for cleaning an electrode, accessible on the inside;
    carrier means having a plurality of supplemental process chambers for and containing electrode means, the supplemental chambers being arranged along the inside of the case so that different portions of the electrode means face different ones of the process chambers in said annular case to be concurrently subjected to different process steps as provided by and in the various chambers; and
    means for stepwise placing the different supplemental chambers and, correspondingly, the different portions of the electrode means sequentially in front of the several process chambers.

2. Apparatus as in claim 1, the carrier being a cylindrical element having a plurality of radial, outwardly facing pockets serving as the supplemental chambers, the pockets provided for facing the process chambers, the electrode means being a plurality of different electrodes disposed in the pockets.

3. Apparatus as in claim 1, the carrier being a cylindrical element having a peripheral groove, the electrode means being a wire disposed in the groove.

4. Apparatus for coordinating process steps for and in a field desorption ionization method, the apparatus comprising:
    an annular arrangement, with inwardly oriented access, of (i) a first chamber for activating an electrode, (ii) a second chamber for depositing analyzing substance onto an activated electrode, (iii) a third chamber for ionizing the substance by means of field desorption ionization, and (iv) a fourth chamber for cleaning an electrode; and
    means for stepwise moving electrode means annularly along said first through fourth chamber so that different portions of the electrode means face each of the chambers simultaneously, and the same portion is stepwise moved past each of the chambers.

5. Apparatus as in claim 4, the electrode means being plural, individual electrodes, there being a rotating carrier for these electrodes.

6. Apparatus as in claim 4, the electrode means being a common wire of which different segments face the chambers at any time, the wire being moved post all of said chambers.

7. Apparatus as in claim 3 or 6, the wire being an endless one.

8. Apparatus as in claim 3 or 6, and including take-up and pay-out means for the wire.

* * * * *